US007084131B2

(12) United States Patent
De Leenheer et al.

(10) Patent No.: US 7,084,131 B2
(45) Date of Patent: Aug. 1, 2006

(54) METHOD FOR PREPARING A POLYDISPERSED SACCHARIDE COMPOSITION AND RESULTING POLYDISPERSED SACCHARIDE COMPOSITION

(75) Inventors: Leen De Leenheer, Tervuren (BE); Karl Booten, Geetbeets (BE)

(73) Assignee: Raffinerie Tirlemontoise S.A. (BE)

( * ) Notice: Subject to any disclaimer, the term of this patent is extended or adjusted under 35 U.S.C. 154(b) by 329 days.

(21) Appl. No.: 10/317,545

(22) Filed: Dec. 12, 2002

(65) Prior Publication Data

US 2003/0186940 A1 Oct. 2, 2003

Related U.S. Application Data

(62) Division of application No. 09/230,769, filed as application No. PCT/BE97/00087 on Jul. 25, 1997, now abandoned.

(30) Foreign Application Priority Data

Aug. 1, 1996 (BE) .................................. 9600676

(51) Int. Cl.
*A61K 31/715* (2006.01)
*A61K 31/70* (2006.01)
*A61K 47/00* (2006.01)
*C07H 1/00* (2006.01)

(52) U.S. Cl. ............................ 514/54; 514/53; 514/23; 536/124; 536/125; 536/123; 536/123.1; 536/123.13; 424/439

(58) Field of Classification Search .................. 514/23, 514/25, 53, 54; 536/122–128; 424/439
See application file for complete search history.

(56) References Cited

U.S. PATENT DOCUMENTS

| 4,871,574 A | 10/1989 | Yamazaki et al. ............ 426/622 |
| 4,990,451 A | 2/1991 | Nakamura et al. ............ 435/201 |
| 5,585,480 A * | 12/1996 | Vogel et al. ................. 536/123 |

FOREIGN PATENT DOCUMENTS

| EP | 04-40074 | * 8/1991 |
| JP | 62-228293 | 10/1987 |
| JP | 06-014792 | 1/1994 |
| JP | 6014792 | 1/1994 |
| WO | 9300067 | 1/1993 |
| WO | 9414970 | 7/1994 |
| WO | 9601849 | 1/1996 |
| WO | 9723511 | 7/1997 |

OTHER PUBLICATIONS

M. Ettalibi et al, Appl. Microbiol. Biotechnol., vol. 26, p. 13-20 (1987) Purification, properties and comparison of invertase, exoinulinases and endoinulinases of *Aspergillus ficuum*, pp. 13-20.
R. Azhari et al, Biotech. and Applied Biochem., vol. 11, 105-117 (1989), Purification and Characterization of endo- and exo-Inulinase, pp. 105-117.
A. Waterhouse, Science and Technology of Fructans, Glossary of Fructans, 1993, pp. 1-7.
Uchiyama, T., Science and Technology of Fructans, Metabolism in Microorganisms Part II, (1993) pp. 169-190.
De Leenheer, Carbohydrate as Organic raw Material, Production and Use of inulin: Industrial reality with a promising future, vol. III (1996) pp. 67-92.
Harada et al, Food Hydrocolloids, Characteristics and applications of a polyfructan synthesized from sucrose by *Aspergillus sydowiconidia*, vol. 7, No. 1, (1993) pp. 23-38.
Aduse-Opoku et al, FEMS Microbiology, Genetic and antigenic comparison of Streptococcus mutans fructosyltransferase and glucan-binding protein, Letters 59, (1989) pp. 279-282.
Chambert et al, Inulin and Inulin-containing crops, Modification of the Transfructosylation . . . , (1993) pp. 259-266.
ORAFTI Product sheet, RAFTILINE HP, Release Apr. 1996.
ORAFTI Product sheet, RAFTILINE P95, Release May 1995.
ORAFTI Product Sheet, RAFTILOSE L95, Release May 1995.
Norman et al, The Production of Fructooligosaccharides from Inulin or Sucrose Using Inulinase or Fructosyltransferase, vol. 36, No. 2 (1989) pp. 103-111.
"Production and use of Inulin: Industrial reality with a Promising Future" Leenheer date and publication unknown; pp. 67-92.
With Actilight, The First Bifidogenic Dietary Fibre, Enter the World of Nutritinal Foods "Nutritional and Technological Properties" SQ/BMIT02/evolution ; 1/01-97; 3 pgs.
"Isolation and identification of O-B-D-fructofuranosyl- . . . " Bruyn et al Elsevier Science Publishers B.V.; 1992; pp. 303-309.
"Inulin and Oligofurctose: Natural Fructans of Plant Origin, Combining Unique Nutritional and Technological Properties" *Food Tech Europe*, 1993, pp. 64-66.
"Pourcentage de Fm" Warcoing, 2002, 2 pgs.
Analysis, by opponent SENSUS, of the composition of Raftilose L95, 1996, 1 pg.
Raftilose P95 product Information and container pictures, 2002, 3 pgs.

(Continued)

*Primary Examiner*—Shengjun Wang
(74) *Attorney, Agent, or Firm*—Hayes Soloway P.C.

(57) ABSTRACT

A method for preparing a polydispersed saccharide composition in which a fructan-containing material is dissolved in water prior to partial enzymatic treatment of the fructans.

20 Claims, No Drawings

OTHER PUBLICATIONS

"Inulin and Inulin-containing Crops" Fuchs, *Studies in Plant Science*, 3, 1993, 9 pgs.

"Science and Technology of Fructans" Suzuki et al., *Science and Technology of Fructans*, 1993, pp. 172, 187, 276, 288 and 300.

"Raftilose and Raftiline as Sugar and Fat Replacers for Frozen Desserts" Franck-Frippiat letter, 1991, 6 pgs.

"Enzymatic Hydrolysis of Inulin-An Alternative Way to Fructose Production" Zittan, *Starch Starke*, 33, 1981, pp. 373-377.

Raffinerie Notre-Dame Certificate of Analysis and Chart, 2 pgs.

Raftilose Technical File, 2 pgs.

Identification of Product, 1994, 7 pgs.

ORAFTI Declaration, 2003, 1 pg.

Analyse Products Finis charts, 1996, 14 pgs.

"Le Sucre, Les Sucres, Les Edulcorants Et Les Glucides De Charge Dans Les I.A.A." Multon, *Collection Sciences et Techniques Argo-Alimentaires*, 1992, pp. 276-277, and 304-305.

* cited by examiner

METHOD FOR PREPARING A POLYDISPERSED SACCHARIDE COMPOSITION AND RESULTING POLYDISPERSED SACCHARIDE COMPOSITION

CROSS-REFERENCE TO RELATED APPLICATION

This application is a Divisional of U.S. application Ser. No. 09/230,769, filed Feb. 1, 1999, now abandoned and claims priority, via PCT/BE97/00087 filed Jul. 25, 1997, from Belgium Application Ser. No. 09600676, filed Jan. 8, 1996.

The present invention relates to a method for preparing a polydispersed saccharide composition low in glucose (G), fructose (F) and saccharose (GF), comprising at least 93.5% by weight relative to the dry matter (DM) of fructo-oligosaccharides consisting of chains of fructose units of formula $F_m$ and of chains of fructose units with a terminal glucose of formula $GF_n$, n and m being between 2 and 20, preferably between 2 and 10, more particularly between 2 and 9, following which a fructan-containing material is subjected to partial hydrolysis.

Such a method is described in patent EP-B-0440074, which relates to a method for the manufacture of an inulo-oligosaccharide product low in glucose, fructose and saccharose. The fructan-containing material is a plant material containing inulin which is subjected, directly after grinding and pasteurization, to an enzymatic treatment using an endo-inulinase. A partially hydrolysed broth is thus obtained which is filtered, and a filtrate is obtained which contains 12.5% of disaccharides, of which 66% is saccharose and 34% inulobiose. Next, the filtrate is treated with an alpha-glucosidase in order to remove the saccharose from it, that is to say that the saccharose is converted to glucose and fructose. The glucose and fructose are then removed by chromatographic separation.

This method has the disadvantage of requiring two enzymatic treatments and one chromatographic separation, which increases its cost and its complexity.

Such a method is also described in the article "Isolation and Identification of O-β-D-fructofuranosyl-(2→1)-O-β-fructofuranosyl-(2→1)-D-fructose, a product of the enzymic hydrolysis of the inulin from *Cichorium intybus*" (A. De Bruyn et al., Carbohydrate Research, 235, pp. 303–308 (1992)). In the method described in this article, inulin extracted from chicory (*Cichorium intybus*) roots is used as fructan-containing material. This inulin is subjected to an enzymatic treatment using an endo-inulinase. A crude syrupy product containing 85% by weight relative to the dry matter (DM) of fructo-oligosaccharides is thus obtained. This crude product is then enriched by chromatography, producing an enriched fraction containing 95% of fructo-oligosaccharides (mainly $GF_n$) and a depleted fraction containing 55% of fructo-oligosaccharides ($GF_n + F_m$).

Although this known method only requires one enzymatic treatment, a chromatographic separation remains essential. Furthermore, the fraction containing 55% of fructo-oligosaccharides is a by-product which has little commercial value.

Another method for producing inulo-oligosaccharides low in glucose, fructose and saccharose is described in Japanese patent application JP-5-21074 (publication JP-6-14792). According to this method, an aqueous solution of 20% inulin, extracted from chicory roots, is subjected to an enzymatic treatment using an endo-enzyme isolated from a Penicillium purpurogenum var. Rubriscerotium culture. After partial hydrolysis, in which the decomposition limit is about 50%, the reducing sugars being calculated as fructose, the solution obtained is purified by treatment with ion-exchange resins and activated charcoal and then the solution is concentrated and the product obtained is dried. Analysis by gel chromatography of the product obtained indicates a content of:

DP1: 1.5%; DP2: 3.3%; DP3: 31.4%; DP4: 26.6%; DP5: 20.4%; DP6: 13.3%; DP>6: 3.5%

The results of a similar partial hydrolysis carried out on inulin by an endo-enzyme obtained from a Penicillium trzebinskii culture indicates a content of:

DP1: 1.3%; DP2: 0.9%; DP3: 26.5%; DP4: 27.6%; DP5: 18.5%; DP6: 14.28%; DP>6: 11.0%

However, in this analysis of the finished product by gel chromatography, the results obtained relate essentially to only the inulo-oligosaccharide fraction having a DP of about 8 maximum, and the fructo-oligosaccharides having a higher DP, although present, are not quantifiable by this method.

The aim of the present invention is to provide a method as described above, which makes it possible to avoid the disadvantages of the methods of the known state of the art.

The present invention relates in particular to a method for preparing a polydispersed saccharide composition low in glucose (G), fructose (F) and saccharose (GF), comprising at least 93.5% by weight relative to the dry matter (DM) of fructo-oligosaccharides consisting of chains of fructoses units of formula $F_m$ and of chains of fructose units with a terminal glucose of formula $GF_n$, n and m being between 2 and 20, preferably between 2 and 10, more particularly between 2 and 9, following which a fructan-containing material is subjected to partial hydrolysis. To this effect, according to the invention, the fructan-containing material comprises fructans with an average degree of polymerization (DP) of at least 7, that is to say greater than or equal to 7, and comprises at most 3.5% by weight relative to the dry matter in total of glucose, fructose and saccharose.

It should be noted that the polydispersed saccharide composition obtained by the method of preparation according to the invention is essentially free of inulo-oligosaccharides having a degree of polymerization of more than 10, preferably more than 9, and that, consequently, its aqueous solution at a concentration of 75%, and normally even of 77%, by weight relative to the dry matter, remains clear during prolonged storage, even for many years, preferably at room temperature. This characteristic gives the product obtained by the method according to the invention a considerable advantage from the technical-commercial point of view compared with the products obtained by a known art method.

Indeed, it has been found that, when the said material is used in the partial hydrolysis, a polydispersed composition is directly obtained which comprises at least 93.5% relative to the DM of fructo-oligosaccharides without requiring a chromatographic separation. Advantageously, the polydispersed composition comprises at least 95% of fructo-oligosaccharides and the said material comprises fructans containing at most 2% of F, G and GF in total.

Preferably, the fructan-containing material comprises at most 1% of F, G and GF in total.

"Fructan" is understood to mean any compound in which one or more fructosyl-fructose linkages constitute most of the linkages, as indicated in the document "Glossary of Fructan Terms" (A. L. Waterhouse et al., Science and Technology of Fructans, pp. 1–7 (1993)), incorporated herein by reference.

"Average degree of polymerization (DP)" is understood to mean the average degree of polymerization ($\overline{DP}_n$) calculated after complete hydrolysis in the following manner:

$$\overline{DP}_n = \frac{\%\text{ total }F}{\%\text{ total }G} + 1$$

It is therefore an average of numbers (see also "Production and use of inulin: Industrial reality with a promising future" (De Leenheer L., Carbohydrate as organic Raw Material Vol. III, pp. 67–92 (1996)) incorporated herein by reference).

"Partial hydrolysis" is understood to mean hydrolysis of the fructan-containing material so as to obtain oligosaccharides whose maximum DP is 20, preferably 10, and more particularly 9, and the content of F+G+GF is less than 5%, and is therefore the opposite of complete hydrolysis which would involve complete degradation to monomers.

Advantageously, in the method according to the invention, the fructans are of the inulin type or of the levan type; the inulin and the levan being characterized by the main presence of fructosyl-fructose linkages of the β-(2→1) type and of the β-(2→6) type respectively (see also the document cited in the paragraph above).

The inulin may be natural inulin or may be produced by microorganisms. In the natural inulin, the DP varies in general from 2 to 60, and depends on the plant origin, the age of the plant, the duration and the conditions of its storage as well as the possible method of extraction. Inulin may be extracted from chicory (*Cichorium intybus*) and dahlia (*Dahlia variabilis*), Jerusalem artichoke (*Helianthus tuberosus*) or globe artichoke (*Cynara scolymus*). The inulin may also be extracted from plants which have been genetically engineered. A method of genetic transformation of such plants is described especially in patent application WO94/14970. The DP of the fructans which is obtained from such plants easily exceeds 10,000.

A natural inulin which can be used in the method according to the invention is for example an inulin having an average DP of 27 and free from G, F and GF. This inulin is marketed under the name SIGMA® with reference I-2255, I-3754 and I-2880 depending on whether the inulin is extracted from chicory, dahlia or Jerusalem artichoke, respectively.

Another natural inulin which can be used is an inulin extracted from chicory which is marketed by ORAFTI under the name Raftiline® HP. This product has an average DP of at least 23 and contains at most, in total relative to the other saccharides, 0.5% of G, F and GF (see also the product sheet dated April 1996 distributed by ORAFTI). The production of such a product is described in Patent Application WO96/01849. According to this application, a solution of inulin extracted from chicory which has a temperature of 65° C. is used as starting material. This solution is brought to a metastable state and then rapidly cooled. Inulin crystals are then added and a fractionated inulin precipitate is obtained in the solution. This precipitate is separated from the solution, washed and dried. The fractionated inulin obtained is free of impurities, has an average DP preferably of between 20 and 40, and contains less than 2% of F, G and GF.

It is obvious that in the method according to the invention, the washed precipitate can be used as it is as raw material.

The DP of an inulin produced by microorganisms may vary up to values of the order of 60,000. Such an inulin is, for example, synthesized from saccharose by *Aspergillus sydowi* conidia in the presence of L-cysteine, as described in the article "Characteristics and Applications of a Polyfructan Synthesized from Sucrose by *Aspergillus sydowi* conidia" (T. Harada et al., Food Hydrocolloids, Vol. 7, No. 1, pp. 23–28 (1993)). The production of a "bacterial" inulin by a fructosyltransferase from *Streptococcus* mutans is described in "Genetic and Antigenic Comparison of Streptococcus mutans Fructosyltransferase and Glucan-binding Protein" (J. Aduse-Opoku, FEMS Microbiology Letters 59, pp. 279–282 (1989)).

Levan is present in nature especially in the Gramineae, but the extraction of levan from these plants is not currently exploited industrially. Levan is mainly obtained by microorganisms, for example from saccharose by the activity of the *Bacillus subtilis* levansucrase enzyme as described in "Modification of the Transfructosylation Activity of *Bacillus subtilis* levansucrase by Solvent Effect and Site-directed Mutagens" (R. Chambert et al., A. Fuchs (Ed.) Inulin and Inulin-containing crops, p. 259 (1993)). It is obvious that levan can also be extracted (as mentioned above for inulin) from plants which have been genetically engineered.

According to the invention, fructan-containing material is dissolved in water prior to the hydrolytic treatment. It is desirable to prepare a solution of 5 to 25% relative to the dry matter, preferably of 10 to 20% relative to the dry matter, of fructans. Nevertheless, in the presence of fructans having a high DP, it is possible that not even 5% of fructans can be dissolved. In any case, it is important to ensure that the fructans are completely solubilized.

The hydrolytic treatment may consist of a partial enzymatic treatment of the fructans. This partial enzymatic treatment of the fructans is well known to persons skilled in the art.

In the case where the fructans are inulin, an enzymatic preparation having an endo-inulinase activity is used. Such preparations are known and can be obtained i.a. from cultures of *Penicillium, Aspergillus, Fusarium* or *Chrysosporium* (see also the document "The production of Fructooligosaccharides from Inulin or Sucrose Using Inulinase or Fructosyltransferase from *Aspergillus ficuum*" (Denpun Kagaku, Vol. 36, No. 2, pp. 103–111 (1989)), incorporated herein by reference).

In the case where the fructans are levan, an enzymatic preparation having an endo-levanase activity is used, as described in the article "Metabolism in Microorganisms, Part II, Biosynthesis and Degradation of Fructans by Microbial Enzymes Other than Levansucrase" (T. Uchiyama, Science and Technology of Fructans, p. 169 (1993)).

It goes without saying that the enzymatic preparations can have only a low exo activity, preferably they are essentially free of exo activity. In general, the enzymatic treatment takes place at a temperature of 58 to 62° C. and at a pH of 5.2 to 5.6, preferably 5.4. The quantity of enzyme units (NOVO method) which is added varies from 0.25 to 6 per gram of dry matter of fructans in the solution. Preferably, 0.4 to 1 unit of enzyme per gram is used. The enzymatic reaction then takes 50 to 2 hours and 30 to 12 hours respectively. When the fructans have a high average DP, for example greater than 50 like in particular the fructans produced by microorganisms, it is recommended to increase, preferably double, the quantity of enzyme units which is used and/or to increase the reaction time. The enzymatic reaction may be stopped in particular by boiling the hydrolysed solution and/or by increasing the pH to 8–9.

It is obvious that the polydispersed saccharide solution which is obtained after the enzymatic treatment is purified (if necessary) by treatments well known per se. Optionally, the solution may be evaporated in order to obtain a syrup having a certain dry matter content, or the solution may be dried, for example, by spray-drying, in order to obtain a powder having the desired particle size.

The present invention also relates to a polydispersed saccharide composition low in glucose (G), fructose (F) and saccharose (GF) comprising at least 93.5%, preferably 95%, by weight relative to the DM of fructo-oligosaccharides consisting of chains of fructose units and chains of fructose units with a terminal glucose, these chains being represented respectively by the formula $F_m$ and the formula $GF_n$, in which n and m are between 2 and 20.

Such a polydispersed saccharide composition is described in Patent EP-B-0440074. In this known composition, the ratio between the nonreducing fructo-oligosaccharides ($GF_n$) and the reducing fructo-oligosaccharides ($F_m$) is not indicated. However, from the method for preparing this composition, it is possible to deduce that most of the fructo-oligosaccharides are $GF_n$.

Such a polydispersed saccharide composition is also described in the article by A. De Bruyn et al. cited above. This known composition comprises mainly fructo-oligosaccharides of formula $GF_n$. This composition is marketed by ORAFTI under the name Raftilose® L95 for the liquid form (syrup) and the name Raftilose® P95 for the solid form (powder) (see also the product sheets dated May 1995 distributed by the company Raffinerie Tirlemontoise).

These known compositions are especially used in the food industry. For example, as food ingredient, they can be easily combined with the other food ingredients without generally affecting the organoleptic and visual properties of the said products. Indeed, these compositions are often used in combination with polyalcohols (being sugar substitutes), in order to enhance certain properties of these polyalcohols, especially the colour of food products which are cooked. Yet, these known compositions have the disadvantage that in some uses, such as pastry making, they do not sufficiently enhance the colour.

In addition, the preparation of these known compositions is complex and expensive.

The aim of the present invention is to also provide a new polydispersed saccharide composition as defined above, which avoids the disadvantages of the known compositions, and which has, in food products, comparable or enhanced organoleptic and visual properties compared with known compositions.

To this effect, the fructo-oligosaccharides comprise more than 43% by weight of fructo-oligosaccharides of formula $F_m$.

Advantageously, the fructo-oligosaccharides comprise more than 45%, preferably more than 50%, by weight of fructo-oligosaccharides of formula $F_m$.

Preferably, the composition according to the invention comprises less than 5%, preferably less than 4%, by weight relative to the total DM of fructose, glucose and saccharose.

Advantageously, the composition of the invention comprises at most 1% by weight relative to the DM of saccharose. Such a composition is therefore more suitable for diabetics.

Furthermore, the composition according to the invention comprises preferably fructo-oligosaccharides consisting of chains of fructose units and chains of fructose units with a terminal glucose, these chains being represented respectively by the formula $F_m$ and the formula $GF_n$, in which n and m are between 2 and 10, more particularly between 2 and 9.

In addition, the polydispersed saccharide composition according to the invention is essentially free of inulo-oligosaccharides having a degree of polymerization of more than 10, preferably of more than 9, and consequently its aqueous solution at a concentration of 75%, and normally even 77%, by weight relative to the dry matter, remains clear during prolonged storage, even for several years, even at room temperature.

The linkages between the fructose units may be of the $\beta$-(2→1) type or of the $\beta$-(2→6) type.

Advantageously, the composition according to the invention is obtained by the method according to the invention defined above.

The compositions according to the invention are particularly suitable for use in human or animal food as bulking agents, sweeteners, low-calorie or weakly cariogenic foods, by bifidogenic products or products which enhance the intestinal flora, products with dietary fibre effect, cholesterol-lowering agents, or alternatively for enhancing the tolerance of food products.

The compositions according to the invention are also particularly suitable for use in pharmaceutical and/or cosmetic products.

Consequently, the present invention also relates to the pharmaceutical and/or cosmetic composition comprising the polydispersed saccharide composition according to the invention.

The following examples illustrate, in a nonlimiting manner, the subject of the present invention.

EXAMPLE 1

The fructan-containing raw material is inulin extracted from chicory having an average DP of 27 and free of F, G and GF. It is an inulin which is marketed under the name SIGMA®. From this inulin, a solution of 10% DM is prepared, the pH of this solution is adjusted to a value of 8 and it is heated for 15 minutes at 90° C. in order to obtain a clear solution. The clear solution is cooled to 65° C. before buffering it to a pH of 5.4.

Next, 0.6 unit of A. Ficuum endo-inulinase enzyme (NOVO) is added per gram of DM of inulin during a 24-hour treatment while the temperature is maintained at 60° C. The enzymatic hydrolysis is stopped by bringing the hydrolysed solution to boiling temperature after having brought the pH to 8. The polydispersed saccharide solution thus obtained is then decolorized and desalted according to methods known to persons skilled in the art. The solvent for the polydispersed solution is then evaporated in order to obtain a syrup of 75% DM which can be easily stored.

The ratio between the various saccharides in the solution obtained was determined by GS (Gas Chromatography) (Table 1).

This ratio is determined for a composition according to the methods of the state of the art described above and used to characterize the Raftilose® L95 products marketed by ORAFTI.

TABLE 1

| POLY-SACCHARIDE | The composition of the invention obtained by the method of the invention % carbohydrate per DM | The composition of the state of the art Raftilose ® L95 % carbohydrate per DM |
|---|---|---|
| Fructose | 1.5 | 0.55 |
| Glucose | 0.1 | 0.04 |
| DFA* | 0.5 | 0.12 |
| Saccharose | 0 | 3.52 |
| $F_2$ | 1.58 | 0.41 |
| $GF_2$ | 0.18 | 4.61 |
| $F_3$ | 32 | 6.51 |
| $GF_3$ | 3.16 | 15.18 |
| $F_4$ | 31.11 | 13.42 |
| $GF_4$ | 5.98 | 21.14 |
| $F_5$ | 10.90 | 8.15 |
| $GF_5$ | 4.57 | 16.81 |
| $F_6$ | 6.50 | 8.56 |
| $GF_6$ | 1.05 | 2.31 |
| $F_7$ | 0.7 | 0.72 |
| $GF_7$ | 0.18 | 0.36 |
| $F_8$ | 0 | 0.21 |
| $GF_8$ | 0 | 0.33 |
| $F_5$ | 0 | 0 |
| DP > 10 | 0 | 0.17 |
| TOTAL | 100 | 100 |

(*DFA = di-fructose anhydride)

EXAMPLE 2

The raw material is inulin marketed by ORAFTI under the name Raftiline® HP. This inulin contains more than 99.5% relative to the DM of the inulin with an average DP of at least 23. A solution of 15% DM is prepared. The pH of the solution is adjusted to a value of 8.5 and it is heated for 20 minutes at 90° C. in order to obtain a clear solution. The other steps of this method are those described in Example 1.

In a manner similar to Example 1, the distribution of the principal saccharides in the product obtained is determined compared with a product obtained according to the state of the art, Raftilose® L95 marketed by Raffinerie Tirlemontoise (Table 2).

TABLE 2

| | The composition of the state of the art Raftilose ® L95 % carbohydrate per DM | The composition of the invention obtained by the method of the invention % carbohydrate per DM |
|---|---|---|
| Fructose | 0.5 | 2.5 |
| Saccharose | 3.6 | 0.3 |
| Glucose | 0.1 | 0.1 |
| $F_3$ | 6.4 | 31.7 |
| $F_m$ | 35 | 78.2 |
| $GF_n$ | 60.8 | 19 |
| FOS | 95.8 | 97.2 |
| $F_m$ % relative to FOS | 37 | 81 |
| $GF_n$ % relative to FOS | 63 | 19 |

The dextrose equivalent, the viscosity and the hygroscopicity were also determined for the composition of the invention and the composition of the state of the art. The dextrose equivalent is about 10 and about 24 respectively. The viscosity was determined for a solution of 77 and 50% DM, respectively, at a respective temperature of 10 and 20° C. (Table 3).

TABLE 3

| Concentration degrees BRIX | Temperature ° C. | The composition of invention obtained by the method of the invention Viscosity mPas | The composition of the art of the state Raftilose ® L95 Viscosity mPas |
|---|---|---|---|
| 77 | 20 | 10,000 | 16,000 |
| 77 | 10 | 24,700 | 57,000 |
| 50 | 20 | 23.5 | 29 |
| 50 | 10 | 32 | 45 |

To compare the water retention of the composition according to the invention with that of the composition according to the state of the art, the changes in weight were determined as a function of the percentage of relative humidity at room temperature. The results are given in Table 4.

TABLE 4

| Relative humidity ° C. | The composition of the state of the art Raftilose ® L95 difference in weigh % | The composition of the invention obtained by the method of the invention difference in weight % |
|---|---|---|
| 23 | −4.2 | −3.4 |
| 44 | −2.0 | −0.2 |
| 66 | +4.7 | +6.0 |
| 80 | +15.7 | +18.2 |

The composition according to the invention is characterized by a greater change in weight, and is therefore more hygroscopic than the composition according to the state of the art. This may be an advantage in some applications, especially in the preparation of cakes.

These two examples demonstrate that the method according to the invention is less complex than the methods according to the state of the art. In addition, the method according to the invention is less expensive, as is the composition according to the invention.

It is evident from Tables 1 and 2 that the ratio $F_m/GF_n$ for the composition according to the invention is different from that for the composition according to the state of the art and that the composition according to the invention may be recommended to diabetics. Tables 3 and 4 demonstrate that the composition according to the invention may also be recommended for certain applications.

EXAMPLE 3

The raw material is inulin obtained by the action of a Streptococcus mutans fructosyltransferase, which contains more than 99.5% relative to the DM of the inulin with an average DP of about 25,000. A solution of 10% DM is prepared. The pH of this solution is adjusted to a value of 8 and it is heated for 20 minutes at 90° C. in order to obtain a clear solution. The clear solution is cooled to 65° C. before buffering it to a pH of 5.4.

Next, 12 units of endo-inulase required are added per gram of DM of inulin, which acts for 2 hours while the temperature is maintained at 60° C. The enzymatic hydrolysis is stopped by boiling the hydrolysed solution after having increased the pH to 8.5–9. The polydispersed saccharide solution thus obtained is then decolorized and desalted in the usual manner.

The ratio between the various saccharides in the solution obtained was determined by HPLC (High Pressure Liquid Chromatography) (Table 5).

TABLE 5

The composition of the invention obtained by the method of the invention
% carbohydrate per DM

| | |
|---|---|
| Fructose | 3.55 |
| Glucose | 0.11 |
| Saccharose | 0.11 |
| Other Dp = 2 | 4 |
| $F_3$ | 30.85 |
| DP = 3 | 23.6 |
| DP = 4 | 11.67 |
| DP = 5 | 26.11 |
| Total | 100 |

EXAMPLE 4

This example relates to the use of the polydispersed saccharide composition (CPS) according to the invention compared with that of the products according to the state of the art in various applications. The appearance, structure, colour, texture, mouth feel and taste of the food compositions obtained are compared. Each application is presented according to the following scheme:
1. Ingredients and proportions
2. Recipe: method of preparation
3. Results (comparison of the three preparations)
   Column 1: The reference, that is to say the application prepared without addition of a polydispersed saccharide composition
   Column 2: The application prepared with the addition of a polydispersed saccharide composition according to the state of the art (composition marketed under the name Raftilose® L95)
   Column 3: The application prepared with the addition of a polydispersed saccharide composition according to the present invention (composition described in Example 2)
4. Conclusions of the comparison. If there is no specific information, the other criteria give identical results Application 1: Chocolate Milk 1. Ingredients Preparation of 300 g of each chocolate milk

| Chocolate milk | 1 | | 2 | | 3 | |
|---|---|---|---|---|---|---|
| | % | g | % | g | % | g |
| Sugar | 5.3 | 15.9 | — | — | — | — |
| Cocoa powder (DE Zaan: D-11-A) | 1.5 | 4.5 | 1.5 | 4.5 | 1.5 | 4.5 |
| Carrageenans granulacta SGI-1 ® | 0.02 | 0.06 | 0.02 | 0.06 | 0.02 | 0.06 |
| Aspartame | — | — | 0.02 | 0.06 | 0.02 | 0.06 |
| CPS | — | — | 7 | 20.51 | 7 | 21.1 |
| Semi-skimmed milk | 92.4 | 277.2 | 90.7 | 272.5 | 90.7 | 272 |
| Total | 100 | 300 | 100 | 300 | 100 | 300 |

2. Method
   Mix the dry products and disperse them in the milk
   Mix for 30 seconds
   Heat 10 seconds at 75° C.
   Cool to refrigerator temperature 3. Results

| | Chocolate milk | | |
|---|---|---|---|
| | 1 | 2 | 3 |
| Taste | quite sweet chocolate taste | quite sweet chocolate taste | quite sweet chocolate taste |
| Mouth feel | less unctuous | more unctuous | unctuous |
| Unctuosity | + | +++ | ++ |

4. Conclusions

No difference in taste is observed between the three preparations. The polydispersed saccharide composition has a positive effect on the unctuosity of the chocolate milk (more unctuous than the reference). The chocolate milk prepared with the polydispersed saccharide composition according to the state of the art is more unctuous than that prepared with the polydispersed composition according to the invention.

Application 2: Vanilla Pudding

1. Ingredients

Preparation of 500 g of each pudding

| Vanilla pudding | 1 | | 2 | | 3 | |
|---|---|---|---|---|---|---|
| | % | g | % | g | % | g |
| Skimmed milk powder | 10.1 | 50.5 | 10.1 | 50.5 | 10.1 | 50.5 |
| Sugar | 10 | 50 | — | — | — | — |
| Maize starch (SF 6304 ®-Cerestar) | 1 | 5 | 1 | 5 | 1 | 5 |
| Stabilizer (Aubygel MR50 ®-Sanofi) | 0.1 | 0.5 | 0.1 | 0.5 | 0.1 | 0.5 |
| β-carotene | 0.01 | 0.05 | 0.01 | 0.05 | 0.01 | 0.05 |
| Aspartame | — | — | 0.03 | 0.15 | 0.03 | 0.15 |
| Vanilla flavour | 0.1 | 0.5 | 0.1 | 0.5 | 0.1 | 0.5 |
| CPS | — | — | 13.3 | 64.9 | 13.3 | 64.9 |
| Whole milk | 75.4 | 377 | 75.4 | 377 | 75.4 | 377 |
| Skimmed milk | 3.3 | 16.5 | — | — | — | — |
| Total | 100 | 500 | 100 | 500 | 100 | 500 |

2. Method
   Mix the dry products except aspartame
   Mix (mixer) the liquids into the milk
   Mix the dry products and the liquids and mix in a mixer for 30 seconds
   Heat for 30 minutes at 95° C.
   Add the aspartame and mix well
   Pour into various small pots
   Cool, place the cover and store at refrigerator temperature 3. Results

|  | Vanilla pudding | | |
|---|---|---|---|
|  | 1 | 2 | 3 |
| Texture (measurement of hardness in g) | flat, fairly liquid (8) | firmer (11.5) | firm (9.5) |
| Taste | sweeter | less sweet | less sweet |
| Mouth feel | less unctuous | unctuous | more unctuous |
| Unctuosity | + | ++ | +++ |

4. Conclusions

The puddings prepared with the polydispersed saccharide composition have a better structure than the reference. They are firmer, more solid. The pudding prepared according to the state of the art is firmer than that containing the product of the invention.

The three puddings are all very creamy, but a difference is noted between them: those containing a polydispersed fructan composition are more creamy than the reference, the pudding containing the product of the invention is more creamy than that prepared with a polydispersed composition according to the state of the art.

The difference from the point of view of mouth feel is however very small between the latter two preparations.

Application 3: Chocolate Mousse

1. Ingredients

|  | Preparation of 500 g of each mousse | | | | | |
|---|---|---|---|---|---|---|
| Chocolate | 1 | | 2 | | 3 | |
| mousse | % | g | % | g | % | g |
| Skimmed milk powder | 7 | 35 | 7 | 35 | 7 | 35 |
| Sugar | 17.5 | 87.5 | — | — | — | — |
| Cocoa powder (De Zaan, D-11-A) | 4 | 20 | 4 | 20 | 4 | 205 |
| Filgel (Quest 9323 ®) | 2.1 | 10.5 | 2.1 | 10.5 | 2.1 | 10.5 |
| Gelatin (Sanofi 80 Bls ®) | 0.5 | 2.5 | 0.5 | 2.5 | 0.5 | 2.5 |
| Aspartame | — | — | 0.05 | 0.25 | 0.05 | 0.25 |
| Cream (35% fat) | 6.3 | 31.5 | 6.3 | 31.5 | 6.3 | 31.5 |
| CPS | — | — | 23.3 | 113.7 | 23.3 | 117.1 |
| Skimmed milk | 62.6 | 313 | 56.8 | 286.7 | 56.8 | 283.4 |
| Total | 100 | 500 | 100 | 500 | 100 | 500 |

2. Method

Mix the dry products except the aspartame and mix (mixer) the liquids

Mix the dry products and the liquids, mix in a mixer for 30 seconds and heat for 30 seconds at 90° C.

Add the aspartame and mix in a mixer for 30 seconds

Cool and place overnight in the refrigerator

Beat 15 minutes using a Hobart beater with "whip"

3. Results

|  | Chocolate mousse | | |
|---|---|---|---|
|  | 1 | 2 | 3 |
| Weight before | 93.5 | 89 | 89 |
| Weight after | 44 | 35.5 | 37 |
| Overrun | 113 | 150 | 140 |
| Texture | rather liquid | quite firm | quite firm |
| Appearance | fairly dark | light-coloured | light-coloured |
| Taste | sweet | sweet, slightly bitter | sweet, slightly bitter |
| Mouth feel | viscous, heavy | very unctuous | very unctuous |

4. Conclusions

The reference chocolate mousse has a very viscous structure, but there is no difference between the mousses made with the polydispersed saccharide composition, either as regards the mouth feel, the taste, structure or the appearance.

Application 4: Bio-yoghurt

1. Ingredients

|  | Preparation of 500 g of each bio-yoghurt. | | | | | |
|---|---|---|---|---|---|---|
|  | 1 | | 2 | | 3 | |
| Bio-yoghurt | % | g | % | g | % | g |
| Whole milk | 94 | 470 | 90.5 | 452.9 | 90.5 | 452.4 |
| Skimmed milk powder | 1 | 5 | 1 | 5 | 1 | 5 |
| CPS | — | — | 3.5 | 17.1 | 3.5 | 17.6 |
| Lactic acid bacteria | 5 | 25 | 5 | 25 | 5 | 25 |
| Total (g) | 100 | 500 | 100 | 500 | 100 | 500 | b 2. Method

Add the whole milk powder and the polydispersed composition to the milk and mix in a mixer for 30 seconds Heat for 8 minutes at 95° C.

Add the lactic acid bacteria and mix well

Put in pots and incubate at 40° C. up to pH 4.8

Cool rapidly and place in a cold chamber (24 hours)

3. Results

The yoghurts were tasted after 24 hours and 48 hours. In both cases, the results are identical.

|  | Bio-yoghurt | | |
|---|---|---|---|
|  | 1 | 2 | 3 |
| Structure | ± liquid | + firm | + firm |
| Texture | + aqueous | + unctuous | + unctuous |
| Taste |  | same throughout | |

4. Conclusions

The yoghurts prepared with the polydispersed saccharide composition are better than the reference, firmer and more unctuous. No difference is noted between the yoghurt prepared with the two polydispersed fructan compositions.

Application 5: Strawberry Sherbet

1. Ingredients

| Preparation of 1000 g of each sherbet | | | |
|---|---|---|---|
| | Strawberry sherbet | | |
| | 1 | 2 | 3 |
| Strawberries | 485 | 485 | 485 |
| Sugar | 200 | — | — |
| CPS | — | 265 | 265 |
| Stabilizer (Grindsted-Fructodan SL64 ®) | 5 | 5 | 5 |
| Aspartame | — | 0.8 | 0.8 |
| Water | 310 | 245 | 245 |
| Total (g) | 1000 | 1000 | 1000 |

2. Method

Thaw and crush (mixer) the strawberries, add the other ingredients (except the aspartame) and mix in a mixer for 20 minutes Heat for 30 seconds at 90° C., add the aspartame (at around 65–70° C.) and cool to 4° C.

Allow to stand overnight at 40° C.

Pass through a Carpigiani (aeration, freezing), package in small pots and place in a deep-freezer for a minimum of 48 hours 3. Results

| | 1 | 2 | 3 |
|---|---|---|---|
| Strawberry sherbet: overrun | | | |
| Weight before | 32 | 33 | 32.5 |
| Weight after | 20 | 20 | 19 |
| Overrun | 61 | 67 | 71 |
| Strawberry sherbet | | | |
| Structure and taste | | same throughout | |
| Mouth feel | + aqueous | unctuous | unctuous |
| Unctuosity | + | ++ | ++ |

4. Conclusions

The sherbets containing the polydispersed saccharide composition are more unctuous than the reference.

The sherbets prepared with the two polydispersed fructan compositions give comparable results.

Application 6: Cake

1. Ingredients

| Cake | 1% | 2% | 3% |
|---|---|---|---|
| Flour | 23.73 | 23.73 | 23.73 |
| Eggs | 24 | 24 | 24 |
| Butter | 20 | 20 | 20 |
| CPS | 0 | 16 | 16 |
| Lactitol | 24 | 12 | 12 |
| Acesulfam K | 0.05 | 0.05 | 0.05 |
| Baking powder V90 ® | 0.2 | 0.2 | 0.2 |
| Baking powder BPpyro ® | 0.02 | 0.02 | 0.02 |
| Water | 8 | 4 | 4 |
| Total | 100 | 100 | 100 |

2. Method

Allow the butter to soften and add the other ingredients

Mix the products using a kitchen utensil for 3 minutes

Pour the whole in a mould and place in an oven at 210° C.

3. Results

The three cakes were baked together for 43 minutes. The cakes containing the polydispersed saccharide composition are better than the reference: they have a brown colour. On the other hand, the reference cake has a pale yellow colour.

There is a difference in colour between the two cakes containing CPS. The cake prepared with the CPS according to the invention has a browner colour compared with that of the cake prepared with the CPS according to the state of the art. The brown colours are a lot more desirable in this type of product.

Application 7: Shortbread

1. Ingredients

| Shortbread | 1% | 2% | 3% |
|---|---|---|---|
| Flour | 45.35 | 45.35 | 45.35 |
| Eggs | 7.6 | 7.6 | 7.6 |
| Butter | 24.2 | 24.2 | 24.2 |
| CPS | 0 | 10.1 | 10.1 |
| Lactitol | 15 | 7.5 | 7.5 |
| Vanilla sugar | 0.8 | 0.8 | 0.8 |
| Acesulfam K | 0.05 | 0.05 | 0.05 |
| Yeast | 0.6 | 0.6 | 0.6 |
| Salt | 0.3 | 0.3 | 0.3 |
| Water | 6.1 | 3.5 | 3.5 |
| Total | 100 | 100 | 100 |

2. Method

Allow the butter to soften and add the ingredients thereto

Mix using a kitchen utensil for homogenizing and pour into moulds

Bake in the oven at 178° C.

3. Results

The three shortbreads were baked together for 14 minutes. The shortbread prepared without the polydispersed saccharide composition has a very pale colour. The other two shortbreads are nicely coloured, the shortbread containing the CPS according to the state of the art has a less pronounced effect.

The invention claimed is:

1. A method for preparing a polydispersed saccharide composition which comprises providing a material containing inulin with an average degree of polymerization equal to or greater than 7, and containing at most 3.5% by weight relative to the dry matter in total of glucose, fructose and saccharose, which is completely solubilized in water, and subjecting said material to partial hydrolysis with an enzymatic preparation having endo-inulinase activity, at a temperature of 58 to 62° C. and at a pH of 5.2 to 5.6, thereby yielding directly, without using a chromatography separation, a polydispersed saccharide composition comprising at least 93.5% by weight, relative to the dry matter, of fructo-oligosaccharides consisting of chains of fructose units of formula $F_m$ and of chains of fructose units with a terminal glucose of formula $GF_n$, n and m being between 2 and 10, comprising more than 43% by weight relative to the dry matter of fructo-oligosaccharides of formula $F_m$ and comprising a glucose, fructose and saccharose content in total of less than 5% by weight relative to the dry matter, an aqueous solution of which at a concentration of 75% by weight relative to the dry matter remains clear during storage at room temperature.

2. The method according to claim 1, wherein the fructo-oligosaccharides obtained correspond to the formula $F_m$ or $GF_n$, in which n and m are between 2 and 9.

3. The method according to claim 1, wherein the polydispersed saccharide composition obtained remains clear in aqueous solution at a concentration of 77%, by weight relative to the dry matter, at room temperature.

4. The method according to claim 1, wherein the polydispersed saccharide composition comprises at least 95% by weight relative to the dry matter of fructo-oligosaccharides comprising more than 45% by weight relative to the dry matter of fructo-oligosaccharides of formula $F_m$ and in that the said material contains at most 2%, by weight relative to the dry matter in total of glucose, fructose and saccharose.

5. The method according to claim 1, wherein the polydispersed saccharide composition comprises at least 95% by weight relative to the dry matter of fructo-oligosaccharides comprising more than 45% by weight relative to the dry matter of fructo-oligosaccharides of formula $F_m$ and in that the said material contains at most 1% by weight relative to the dry matter in total of glucose, fructose and saccharose.

6. The method according to claim 1, wherein the hydrolysis is carried out using an enzyme preparation containing 0.25 to 12 enzyme units, as determined by the NOVO method, per gram of dry matter of inulin.

7. The method according to claim 1, wherein the polydispersed saccharide composition obtained after partial hydrolysis is thereafter decolorized and desalted.

8. The method according to claim 6, wherein the enzyme preparation contains 0.25 to 6 enzyme units per gram of dry matter of fructans.

9. A method for preparing polydispersed saccharide composition which comprises providing a source material containing inulin with an average degree of polymerisation equal to or greater than 7, and containing at most 3.5% by weight relative to the dry matter in total of glucose, fructose and saccharose, said source material being obtained from a solution of inulin extracted from chicory that has a temperature of 65° C. and is brought to a metastable state and then is rapidly cooled, seeded with inulin crystals and is then yielding a fractionated precipitate that is separated from the solution, washed and optionally dried, thus yielding the source material, and wherein said source material is then completely solubilized in water, and subjecting said source material to a partial hydrolysis with an enzymatic preparation having endo-inulinase activity, at a temperature of 58 to 62° C. and at a pH of 5.2 to 5.6, thereby yielding directly, without using a chromatography separation, a polydispersed saccharide composition comprising at least 93.5% by weight, relative to the dry matter, of fructo-oligosaccharides consisting of chains of fructose units of formula $F_m$ and of chains of fructose units with a terminal glucose of formula $GF_n$, n and m being between 2 and 10, comprising more than 43% by weight relative to the dry matter of fructo-oligosaccharides of formula $F_m$ and comprising a glucose, fructose and saccharose content in total of less than 5% by weight relative to the dry matter, an aqueous solution of which at a concentration of 75% by weight relative to the dry matter remains clear during storage at room temperature.

10. The method according to claim 9, wherein the source material has an average degree of polymerisation between 20 and 40, and contains less than 2% of fructose, glucose and sucrose.

11. The method according to claim 1, wherein the partial hydrolysis is conducted at a temperature of 60° C.

12. The method according to claim 1, wherein the partial hydrolysis is conducted at a pH of 5.4.

13. The method according to claim 1, wherein the partial hydrolysis is conducted for a duration of 2 to 50 hours.

14. The method according to claim 1, wherein the partial hydrolysis is conducted for a duration of 12 to 30 hours.

15. The method according to claim 1, wherein the partial hydrolysis is conducted for a duration of 24 hours.

16. The method of claim 9, wherein the partial hydrolysis is conducted at a temperature of 60° C.

17. The method of claim 9, wherein the partial hydrolysis is conducted at a pH of 5.4.

18. The method of claim 9, wherein the partial hydrolysis is conducted for a duration of 2 to 50 hours.

19. The method of claim 9, wherein the partial hydrolysis is conducted for a duration of 12 to 30 hours.

20. The method of claim 9, wherein the partial hydrolysis is conducted for a duration of 24 hours.

* * * * *